(12) United States Patent
Chan et al.

(10) Patent No.: US 11,913,659 B2
(45) Date of Patent: Feb. 27, 2024

(54) SYSTEMS AND METHODS FOR MONITORING OPERATION OF AN HVAC SYSTEM

(71) Applicant: Honeywell International Inc., Charlotte, NC (US)

(72) Inventors: Foong Yeen Chan, Petaling (MY); Zhongshengyun Gao, Shanghai (CN); Prabhat Ranjan, Bangalore (IN); Bhavesh Gupta, Niantic, CT (US); Gutha Stalin Sanghamitra, Bangalore (IN); Ashu Rawat, Redmond, WA (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 236 days.

(21) Appl. No.: 17/346,885

(22) Filed: Jun. 14, 2021

(65) Prior Publication Data
US 2021/0389007 A1 Dec. 16, 2021

Related U.S. Application Data

(60) Provisional application No. 63/039,389, filed on Jun. 15, 2020.

(51) Int. Cl.
*F24F 11/38* (2018.01)
*G01N 33/00* (2006.01)
(Continued)

(52) U.S. Cl.
CPC ............ *F24F 11/38* (2018.01); *G01N 33/004* (2013.01); *G06T 11/206* (2013.01); *F24F 2110/70* (2018.01)

(58) Field of Classification Search
CPC .. F24F 11/38; F24F 11/30; F24F 11/52; F24F 2110/70; F24F 2110/20; F24F 2110/30;
(Continued)

(56) References Cited

U.S. PATENT DOCUMENTS 8,473,080 B2 6/2013 Seem et al.
9,002,532 B2 4/2015 Asmus
(Continued)

OTHER PUBLICATIONS

Building Automation System in Michigan, Johnson Heating and Cooling, L.L.C., www.cooljohnson.com/Building-Automation-Systems-Michigan/Macomb-County-Michigan/Building-Automation-Confidential-Customer.html, 4 pages, Accessed Nov. 21, 2022.
(Continued)

*Primary Examiner* — Jeffrey P Aiello
(74) *Attorney, Agent, or Firm* — Seager, Tufte & Wickhem, LLP (57) ABSTRACT

A computer system provides a method for analyzing various parameters, variables and/or conditions associated with the operation of HVAC systems. Some example computer systems display a coordinate system with multiple graphs of variables and conditions having disparate units of measure, such as degrees Centigrade, percent, ppm, on/off, etc. In some examples, variables and conditions with similar units of measure are grouped together. The groups of similar units are plotted along different segments of the coordinate system's y-axis. The segments and their respective graphs of similar units are distributed vertically, one above the other. All of the graphs, however, share a common x-axis, which is labeled in units of time. This makes it easier to visually compare multiple, disparate variables and conditions at particular points in time. When an HVAC related problem occurs, the visual comparisons can help identify the problem and its source.

19 Claims, 8 Drawing Sheets

(51) Int. Cl.
*G06T 11/20* (2006.01)
*F24F 110/70* (2018.01)

(58) Field of Classification Search
CPC .. F24F 11/62; F24F 11/46; F24F 11/63; F24F 11/58; F24F 11/56; F24F 11/47; G01N 33/0006; G01N 33/004; G01N 1/2273; G01N 25/18; G01N 1/26; G06T 11/206; G06T 2200/24; G06T 11/001; G06T 11/60; Y02B 30/70; Y02B 70/30; Y02B 70/3225; Y02B 70/30; G06Q 50/06; G06Q 10/06; G06Q 10/10; G05B 15/02; G05B 2219/2642; G05B 23/0221; G05B 2219/2614; G01K 13/00; G01K 17/20
USPC ...... 340/540, 870.01; 700/83, 108, 276–278, 700/282, 286, 291, 295, 297; 702/1, 45, 702/57, 60–62, 130, 138, 176, 179, 702/181–184, 188–189
See application file for complete search history.

(56) References Cited

U.S. PATENT DOCUMENTS

| | | | |
|---|---|---|---|
| 9,235,657 B1 | 1/2016 | Wenzel et al. | |
| 9,256,702 B2 | 2/2016 | Elbsat et al. | |
| 9,322,566 B2 | 4/2016 | Wenzel et al. | |
| 9,355,069 B2 | 5/2016 | Elbsat et al. | |
| 9,436,179 B1 | 9/2016 | Turney et al. | |
| 9,447,985 B2 | 9/2016 | Johnson, Jr. | |
| 9,568,204 B2 | 2/2017 | Asmus et al. | |
| 9,581,985 B2 | 2/2017 | Walser et al. | |
| 9,606,520 B2 | 3/2017 | Noboa et al. | |
| 9,612,601 B2 | 4/2017 | Beyhaghi et al. | |
| 9,696,054 B2 | 7/2017 | Asmus | |
| 9,778,639 B2 | 10/2017 | Boettcher et al. | |
| 9,798,336 B2 | 10/2017 | Przybylski | |
| 9,852,481 B1 | 12/2017 | Turney et al. | |
| 9,982,903 B1 | 5/2018 | Ridder et al. | |
| 10,007,259 B2 | 6/2018 | Turney et al. | |
| 10,055,114 B2 * | 8/2018 | Shah | G06F 3/04847 |
| 10,101,730 B2 | 10/2018 | Wenzel et al. | |
| 10,101,731 B2 | 10/2018 | Asmus et al. | |
| 10,175,681 B2 | 1/2019 | Wenzel et al. | |
| 10,222,083 B2 | 3/2019 | Drees et al. | |
| 10,282,796 B2 | 5/2019 | Elbsat et al. | |
| 10,288,306 B2 | 5/2019 | Ridder et al. | |
| 10,317,864 B2 | 6/2019 | Boettcher et al. | |
| 10,359,748 B2 | 7/2019 | Elbsat et al. | |
| 10,386,820 B2 | 8/2019 | Wenzel et al. | |
| 10,402,767 B2 * | 9/2019 | Noboa | G06Q 10/0635 |
| 10,514,178 B2 | 12/2019 | Willmott et al. | |
| 10,520,210 B2 | 12/2019 | Park et al. | |
| 10,544,955 B2 | 1/2020 | Przybylski | |
| 10,558,178 B2 | 2/2020 | Willmott et al. | |
| 10,559,180 B2 | 2/2020 | Pourmohammad et al. | |
| 10,559,181 B2 | 2/2020 | Pourmohammad et al. | |
| 10,600,263 B2 | 3/2020 | Park et al. | |
| 10,605,477 B2 | 3/2020 | Ridder | |
| 10,619,882 B2 | 4/2020 | Chatterjee et al. | |
| 10,627,124 B2 | 4/2020 | Walser et al. | |
| 10,673,380 B2 | 6/2020 | Wenzel et al. | |
| 10,678,227 B2 | 6/2020 | Przybylski et al. | |
| 10,706,375 B2 | 7/2020 | Wenzel et al. | |
| 10,726,711 B2 | 7/2020 | Subramanian et al. | |
| 10,732,584 B2 | 8/2020 | Elbsat et al. | |
| 10,767,885 B2 | 9/2020 | Przybylski et al. | |
| 10,775,988 B2 | 9/2020 | Narain et al. | |
| 10,796,554 B2 | 10/2020 | Vincent et al. | |
| 10,809,682 B2 | 10/2020 | Patil et al. | |
| 10,809,705 B2 | 10/2020 | Przybylski | |
| 10,824,125 B2 | 11/2020 | Elbsat et al. | |
| 10,854,194 B2 | 12/2020 | Park et al. | |
| 10,871,298 B2 | 12/2020 | Ridder et al. | |
| 10,871,756 B2 | 12/2020 | Johnson, Jr. et al. | |
| 10,876,754 B2 | 12/2020 | Wenzel et al. | |
| 10,890,904 B2 | 1/2021 | Turney et al. | |
| 10,900,686 B2 | 1/2021 | Willmott et al. | |
| 10,901,446 B2 | 1/2021 | Nesler et al. | |
| 10,908,578 B2 | 2/2021 | Johnson, Jr. et al. | |
| 10,909,642 B2 | 2/2021 | Elbsat et al. | |
| 10,915,094 B2 | 2/2021 | Wenzel et al. | |
| 10,917,740 B1 | 2/2021 | Scott et al. | |
| 10,921,768 B2 | 2/2021 | Johnson, Jr. et al. | |
| 10,921,972 B2 | 2/2021 | Park et al. | |
| 10,921,973 B2 | 2/2021 | Park et al. | |
| 10,928,790 B2 | 2/2021 | Mueller et al. | |
| 10,948,884 B2 | 3/2021 | Beaty et al. | |
| 10,949,777 B2 | 3/2021 | Elbsat et al. | |
| 10,955,800 B2 | 3/2021 | Burroughs et al. | |
| 10,956,842 B2 | 3/2021 | Wenzel et al. | |
| 10,962,945 B2 | 3/2021 | Park et al. | |
| 10,969,135 B2 | 4/2021 | Willmott et al. | |
| 11,002,457 B2 | 5/2021 | Turney et al. | |
| 11,009,252 B2 | 5/2021 | Turney et al. | |
| 11,010,846 B2 | 5/2021 | Elbsat et al. | |
| 11,016,648 B2 | 5/2021 | Fala et al. | |
| 11,016,998 B2 | 5/2021 | Park et al. | |
| 11,022,947 B2 | 6/2021 | Elbsat et al. | |
| 11,024,292 B2 | 6/2021 | Park et al. | |
| 11,036,249 B2 | 6/2021 | Elbsat | |
| 11,038,709 B2 | 6/2021 | Park et al. | |
| 11,042,139 B2 | 6/2021 | Deshpande et al. | |
| 11,042,924 B2 | 6/2021 | Asmus et al. | |
| 11,061,424 B2 | 7/2021 | Elbsat et al. | |
| 11,068,821 B2 | 7/2021 | Wenzel et al. | |
| 11,070,389 B2 | 7/2021 | Schuster et al. | |
| 11,073,976 B2 | 7/2021 | Park et al. | |
| 11,080,289 B2 | 8/2021 | Park et al. | |
| 11,080,426 B2 | 8/2021 | Park et al. | |
| 11,086,276 B2 | 8/2021 | Wenzel et al. | |
| 11,094,186 B2 | 8/2021 | Razak | |
| 11,108,587 B2 | 8/2021 | Park et al. | |
| 11,131,473 B2 | 8/2021 | Risbeck et al. | |
| 11,113,295 B2 | 9/2021 | Park et al. | |
| 11,119,458 B2 | 9/2021 | Asp et al. | |
| 11,120,012 B2 | 9/2021 | Park et al. | |
| 11,150,617 B2 | 10/2021 | Ploegert et al. | |
| 11,151,983 B2 | 10/2021 | Park et al. | |
| 11,156,978 B2 | 10/2021 | Johnson, Jr. et al. | |
| 11,156,996 B2 | 10/2021 | Schuster et al. | |
| 11,158,306 B2 | 10/2021 | Park et al. | |
| 11,182,047 B2 | 11/2021 | Nayak et al. | |
| 11,195,401 B2 | 12/2021 | Pourmohammad | |
| 11,217,087 B2 | 1/2022 | Pelski | |
| 11,226,126 B2 | 1/2022 | Przybylski et al. | |
| 11,243,523 B2 | 2/2022 | Llopis et al. | |
| 11,268,715 B2 | 3/2022 | Park et al. | |
| 11,268,996 B2 * | 3/2022 | Vitullo | G01R 22/10 |
| 11,269,505 B2 | 3/2022 | Fala et al. | |
| 11,272,011 B1 | 3/2022 | Laughton et al. | |
| 11,272,316 B2 | 3/2022 | Scott et al. | |
| 11,275,348 B2 | 3/2022 | Park et al. | |
| 11,275,363 B2 | 3/2022 | Przybylski et al. | |
| 11,281,169 B2 | 3/2022 | Chatterjee et al. | |
| 11,288,754 B2 | 3/2022 | Elbsat et al. | |
| 11,314,726 B2 | 4/2022 | Park et al. | |
| 11,314,788 B2 | 4/2022 | Park et al. | |
| 11,334,044 B2 | 5/2022 | Goyal | |
| 11,353,834 B2 | 6/2022 | Mueller et al. | |
| 11,356,292 B2 | 6/2022 | Ploegert et al. | |
| 11,360,451 B2 | 6/2022 | Pancholi et al. | |
| 11,361,123 B2 | 6/2022 | Ploegert et al. | |
| 2004/0262410 A1 * | 12/2004 | Hull | F24F 11/30 236/94 |
| 2012/0262472 A1 * | 10/2012 | Garr | G06T 11/206 345/589 |
| 2014/0324229 A1 * | 10/2014 | Leen | G05D 23/19 700/276 |
| 2016/0061473 A1 | 3/2016 | Johnson, Jr. | |
| 2018/0259927 A1 * | 9/2018 | Przybylski | G06F 9/451 |
| 2019/0302157 A1 * | 10/2019 | Vitullo | G01K 17/20 |
| 2020/0256571 A1 | 8/2020 | Johnson, Jr. et al. | |
| 2021/0010701 A1 | 1/2021 | Suindykov et al. | |

(56) References Cited

U.S. PATENT DOCUMENTS

| | | |
|---|---|---|
| 2021/0011443 A1 | 1/2021 | Mcnamara et al. |
| 2021/0011444 A1 | 1/2021 | Risbeck et al. |
| 2021/0356927 A1 | 11/2021 | Johnson, Jr. et al. |
| 2021/0364181 A1 | 11/2021 | Risbeck et al. |
| 2021/0373519 A1 | 12/2021 | Risbeck et al. |
| 2022/0011731 A1 | 1/2022 | Risbeck et al. |
| 2022/0113045 A1 | 4/2022 | Gamroth et al. |
| 2022/0137580 A1 | 5/2022 | Burroughs et al. |

OTHER PUBLICATIONS

Building Automation System Waterford Michignan 48328 JLA, Johnson Heating and Cooling L.L.C., www.cooljohnson.com/Building-Automation-Systems-Michigan/Waterford-Michigan/Building-Automation-System-JLA.html, 3 pages, Accessed Nov. 21, 2022.

Building Automation Systems Waterford Michigan 48330 SJMO, Johnson Heating and Cooling, L.L.C., www.cooljohnson.com/Building-Automation-Systems-Michigan/Waterford-Michigan/Building-Automation-Systems-SJMO.html, 2 pages, Accessed Nov. 21, 2022.

Building Automation Systems Waterford Michigan 48329 WIM, Johnson Heating and Cooling L.L.C., www.cooljohnson.com/Building-Automation-Systems-Michigan/Building-Automation-Systems-WIM.html, 3 pages, accessed Nov. 21, 2022.

Building Automation Clawson Michigan 2.0, Johnson Heating and Cooling L.L.C., www.cooljohnson.com/Building-Automation-Systems-Michigan/Clawson-Michigan/Building-Automation-Clawson-Manor-2.html, 6 pages, Accessed Nov. 21, 2022.

Building Automation in Detroit—Mosaic Christian, Johnson Heating and Cooling L.L.C., www.cooljohnson.com/Building-Automation-Systems-Michigan/Detroit/Mosaic-Christian.html, 5 pages, Accessed Nov. 21, 2022.

Building Automation in Michigan—Divine Grace, Johnson Heating and Cooling L.L.C., www.cooljohnson.com/Building-Automation-Systems-Michigan/Oakland-County-Michigan/Building-Automation-Divine-Grace.html, 3 pages, Accessed Nov. 21, 2022.

Building Automation System Plymouth, Michigan, Johnson Heating and Cooling L.L.C., www.cooljohnson.com/Building-Automation-Systems-Michigan/Plymouth-Michigan/Building-Automation-System-Plymouth-Michigan.html, 8 pages, Accessed Nov. 21, 2022.

Building Automation Systems Shelby Michigan 48316 SG, Johnson Heating and Cooling L.L.C., www.cooljohnson.com/Building-Automation-Systems-Michigan/Shelby-Township-Michigan/Building-Automation-Systems-SG.html, 3 pages, Accessed Nov. 21, 2022.

Building Automation System St. Clair County, Michigan, Johnson Heating and Cooling L.L.C., www.cooljohnson.com/building-Automation-Systems-Michigan/St-Clair-Michigan/Building-Automation-system-St-Clair-Michigan.html, 4 pages, Accessed Nov. 21, 2022.

Building Automation System Troy Michigan Oakland Mall, Johnson Heating and Cooling L.L.C., www.cooljohnson.com/Building-Automation-Systems-Michigan/Troy Michigan/Building-Automation-System-Oakland-Mall.html, 4 pages, Accessed Nov. 21, 2022.

Building Automation System Waterford Michigan 48327 Excel, Johnson Heating and Cooling L.L.C., www.cooljohnson.com/Building-Automation-Systems-Michigan/Waterford-Michigan/Building-Automation-System-excel.html, 2 pages, Accessed Nov. 22, 2022.

Building Automation System Romeo Michigan 48065 RomeoPR, Johnson Heating and Cooling, L.L.C., www.cooljohnson.com/Building-Automation-Systems-Michigan/Romeo-Michigan/Building-Automation-System-RomeoPR.html, 2 pages, Accessed Nov. 21, 2022.

Johnson, Jr., "Cooling Logic™: Changing the Way You Cool," Johnson Solid State, LLC, 12 pages, Nov. 7, 2018.

Building Automation System Clawson Michigan Clawson Manor, Johnson Heating and Cooling L.L.C., www.cooljohnson.com/building-Automation-Systems-michigan/clawson-Michigan/building-Automation-System-Clawson-Manor.html, 3 pages, Accessed Nov. 21, 2022.

Johnson, Jr., "CoolingLogic™ A Method to increase HVAC System Efficiency And Decrease Energy Consumption," A White Paper, Johnson Solid State, L.L.C., 51 pages, Sep. 24, 2016.

Johnson, Jr., "CoolingLogic™: Mosaic Christian Church A Case Study," 140 pages, Feb. 2, 2019.

Rosenberg, "Analyzing Air Handling Unit Efficiency," Onset Computer Corporation, Bourne, Massachusetts, 24 pages, 2014. www.onsetcomp.com.

Johnson Controls Develops Industry-first AI Driven Digital Solution to Manage Clean Air, Energy, Sustainability, Comfort and Cost in Buildings, 7 pages, 2022. Accessed Aug. 29, 2022.

Johnson Controls and Microsoft Announce Global Collaboration, Launch Integration between Open Blue Digital Twin and Azure Digital Twins, 7 pages, 2022. Accessed Aug. 29, 2022.

Open Blue Companion Desktop User Guide, Johnson Controls, 18 pages, 2022.

Open Blue Digital Twin:Designed for Buildings. Infused with AI, Johnson Controls, 17 pages, 2022. Accessed Aug. 29, 2022.

Open Blue Enterprise Manager User Guide, Johnson Controls, Release 3.1, 72 pages, Jan. 28, 2021.

Open Blue Enterprise Manager User Guide, Johnson Controls, Release 4.0, 78pages, Nov. 29, 2021.

Open Blue Location Manager User Guide, Johnson Controls, Release 2.4.7, 28 pages, Jul. 20, 2022.

Open Blue Enterprise Manager, Optimize Building Portfolio Performance with Advanced Data Analytics and AI, Johnson Controls, 20 pages, Accessed Aug. 29, 2022.

Open Blue Platform, Make Smarter, Faster, More Data-Driven Decisions, Johnson Controls, 15 pages, 2022. Accessed Aug. 29, 2022.

Open Blue, Now, Spaces have Memory and Identity, Johnson Controls, 20 pages, 2022. Accessed Feb. 10, 2022.

Open Blue Enterprise Manager User Guide, Johnson Controls, 108 pages, Release 4.1.3, 2022, Accessed Aug. 29, 2022.

Risbeck et al; "Modeling and Multiobjective Optimization of Indoor Airborne Disease Transmission Risk and Associated Energy Consumption for Building HVAC Systems," Energy and Buildings, vol. 253, 24 pages, 2021.

Sinha et al; "Balance Infection Risk, Sustainability and Comfort with Open Blue," Johnson Controls, 2 pages, 2021.

* cited by examiner

FIG. 8

SYSTEMS AND METHODS FOR MONITORING OPERATION OF AN HVAC SYSTEM

This application claims the benefit of U.S. Provisional Application No. 63/039,389, filed Jun. 15, 2020, which is hereby incorporated by reference.

TECHNICAL FIELD

The disclosure relates generally to facility management systems, and more particularly to methods and systems for analyzing various parameters, variables and/or conditions pertaining to the operation of HVAC systems.

BACKGROUND

Heating, ventilating and air conditioning systems are commonly known as HVAC systems. HVAC systems often include equipment such as refrigerant compressors, heat exchangers, blowers/fans, filters, valves and dampers. Such equipment can be arranged in various configurations and often operated in different modes to control the comfort and quality of a facility's indoor air.

Facility management systems typically include a computer system for monitoring and/or controlling the operation of HVAC systems as well as monitoring and/or adjusting the temperature and various air quality conditions of the facility. Some examples of monitored parameters, variables and conditions associated with HVAC system or the facilities they serve include room temperature, setpoint temperature, relative humidity, concentration of carbon dioxide in the air, on/off state of various HVAC equipment, operating mode of HVAC equipment, and room occupancy.

SUMMARY

The present disclosure generally pertains systems and methods for analyzing various parameters, variables and/or conditions associated with the operation of HVAC systems. In some examples, a computer system displays a coordinate system with multiple graphs of variables and conditions having disparate units of measure, such as degrees Centigrade, percent, ppm, on/off, etc. In some examples, variables and conditions with similar units of measure are grouped together. The groups of similar units are plotted along different segments of the coordinate system's y-axis (ordinate). So, the segments and their respective graphs of similar units are distributed vertically, one above the other. All of the graphs, however, share a common x-axis (abscissa), which is labeled in units of time. This makes it easier to visually compare multiple, disparate variables and conditions at particular points in time. When an HVAC related problem occurs, the visual comparisons can help identify the problem and its source.

In some examples of the disclosure, a method for monitoring operations of an HVAC system includes receiving at least a first time-series of data and a second time-series of data each corresponding to different parameters associated with the operation of the HVAC system. The method includes displaying a coordinate system on a display, wherein the coordinate system includes an x-axis extending horizontally and a y-axis extending vertically. Time labels are displayed along the x-axis. The y-axis is segmented into multiple segments including at least a first segment and a second segment. The second segment is below the first one. A first set of labels in terms of a first unit of measure are displayed along the first segment, and a second set of labels in terms of a second unit of measure (different from the first) are displayed along the second segment. A first running graph of the first time-series of data expressed in the first unit of measure is displayed in alignment with the first segment of the y-axis. A second running graph of the second time-series of data expressed in the second unit of measure is displayed in alignment with the second segment of the y-axis.

In some examples of the disclosure, a computer readable medium causes a computer system to receive at least a first time-series of data and a second time-series of data, each corresponding to different parameters associated with the operation of an HVAC system. Each of the first and second time-series of data has a corresponding unit of measure. The computer system displays a coordinate system that includes an x-axis extending horizontally and a y-axis extending vertically. A set of time labels are displayed along the x-axis. The y-axis includes a first segment with a first set of labels in terms of a first unit of measure. The y-axis includes a second segment with a second set of labels in terms of a second unit of measure that is different from the first unit of measure. The computer system displays a first running graph in alignment with the first segment of the y-axis, wherein the first running graph is of the first time-series of data expressed in the first unit of measure. The computer system displays a second running graph in alignment with the second segment of the y-axis, wherein the second running graph is of the second time-series of data expressed in the second unit of measure.

In some examples of the disclosure, a computing system includes a display and an input for receiving a plurality of time-series of data each corresponding to one of a plurality of parameters associated with an operation of an HVAC system. Each of the plurality of time-series of data is expressed in terms of a corresponding unit of measure. The computing system further includes a processor operatively coupled to the display and the input. The processor displays a coordinate system on the display, wherein the coordinate system includes an x-axis extending horizontally and a y-axis extending vertically. The processor displays a set of time labels along the x-axis. The processor segments the y-axis into a plurality of segments. The processor displays a first set of labels along a first segment of the plurality of segments of the y-axis in terms of a first unit of measure. The processor displays a second set of labels along a second segment of the plurality of segments of the y-axis in terms of a second unit of measure different from the first unit of measure. The processor identifies a first one of the plurality of time-series of data that is expressed in the first unit of measure, and display the first one of the plurality of time-series of data as a first running graph aligned with the first segment of the y-axis. The processor identifies a second one of the plurality of time-series of data that is expressed in the second unit of measure, and display the second one of the plurality of time-series of data as a second running graph aligned with the second segment of the y-axis. The processor identifies a third one of the plurality of time-series of data that is expressed in the first unit of measure, and displays the third one of the plurality of time-series of data as a third running graph aligned with the first segment of the y-axis. The processor identifies a fourth one of the plurality of time-series of data that varies with respect to the second unit of measure, and display the fourth one of the plurality of time-series of data as a fourth running graph aligned with the second segment of the y-axis. The processor identifies one or more of the plurality of time-series of data that correspond to equipment status of the HVAC system, and displays one of the plurality of time-series of data that correspond to equipment status of the HVAC system as a fifth running graph aligned with a third segment of the plurality of segments of the y-axis. The processor displays a visual alignment tool with a vertical line that is movable along the x-axis and each of the first and second running graphs. The processor accepts input from a user that causes the visual alignment tool to move the vertical line horizontally along the x-axis. The processor accepts a timeframe from the user and aligns the x-axis of the coordinate system with the received timeframe.

The preceding summary is provided to facilitate an understanding of some of the features of the present disclosure and is not intended to be a full description. A full appreciation of the disclosure can be gained by taking the entire specification, claims, drawings and abstract as a whole.

BRIEF DESCRIPTION OF THE DRAWINGS

The disclosure may be more completely understood in consideration of the following description of various illustrative embodiments of the disclosure in connection with the accompanying drawings in which.

While the disclosure is amendable to various modifications and alternative forms, specifics thereof have been shown by way of example in the drawings and will be described in detail. It should be understood, however, that the intention is not to limit the disclosure to the particular illustrative embodiments described herein. On the contrary, the intention is to cover all modifications, equivalents, and alternatives falling within the spirit and scope of the disclosure.

DESCRIPTION

The following description should be read with reference to the drawings wherein like reference numerals indicate like elements throughout the several views. The description and drawings show several examples that are meant to be illustrative of the disclosure.

The disclosure pertains to methods and systems for analyzing various parameters, variables and/or conditions associated with the operation of HVAC systems. In some examples, a computer system displays a coordinate system with multiple graphs of variables and conditions having disparate units of measure, such as degrees Centigrade, percent, ppm, on/off, etc. In some examples, variables and conditions with similar units of measure are grouped together. The groups of similar units are plotted along different segments of the coordinate system's y-axis (ordinate). So, the segments and their respective graphs of similar units are distributed vertically, one above the other. All of the graphs, however, share a common x-axis (abscissa), which is labeled in units of time. This makes it easy to visually compare multiple, disparate variables and conditions at a particular point in time. When an HVAC related problem occurs, the visual comparisons can help identify the problem and its source.

Figure 1:
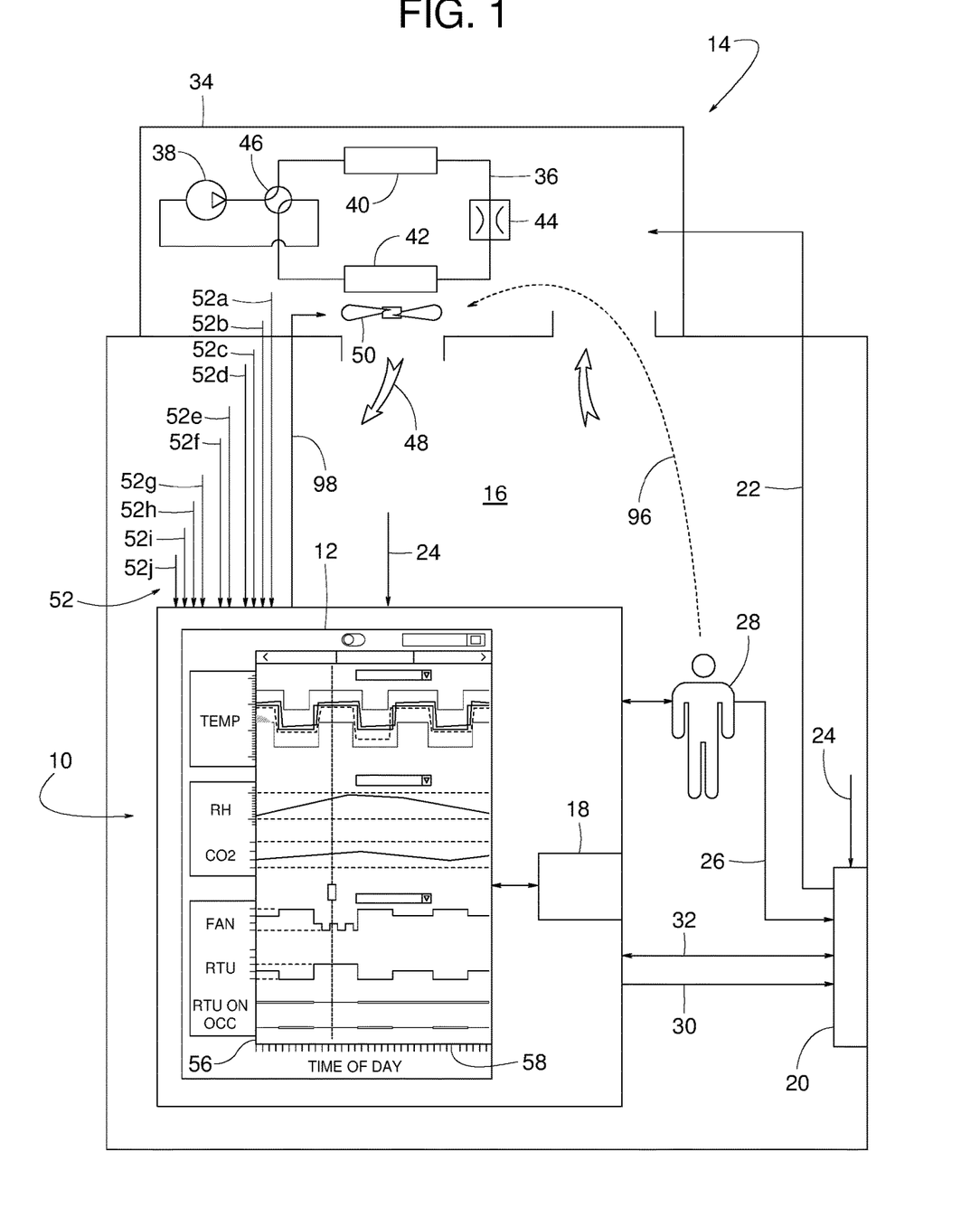
FIG. 1 is a schematic block diagram of an example computer system for monitoring conditions associated with an example HVAC system.
Figure 4:
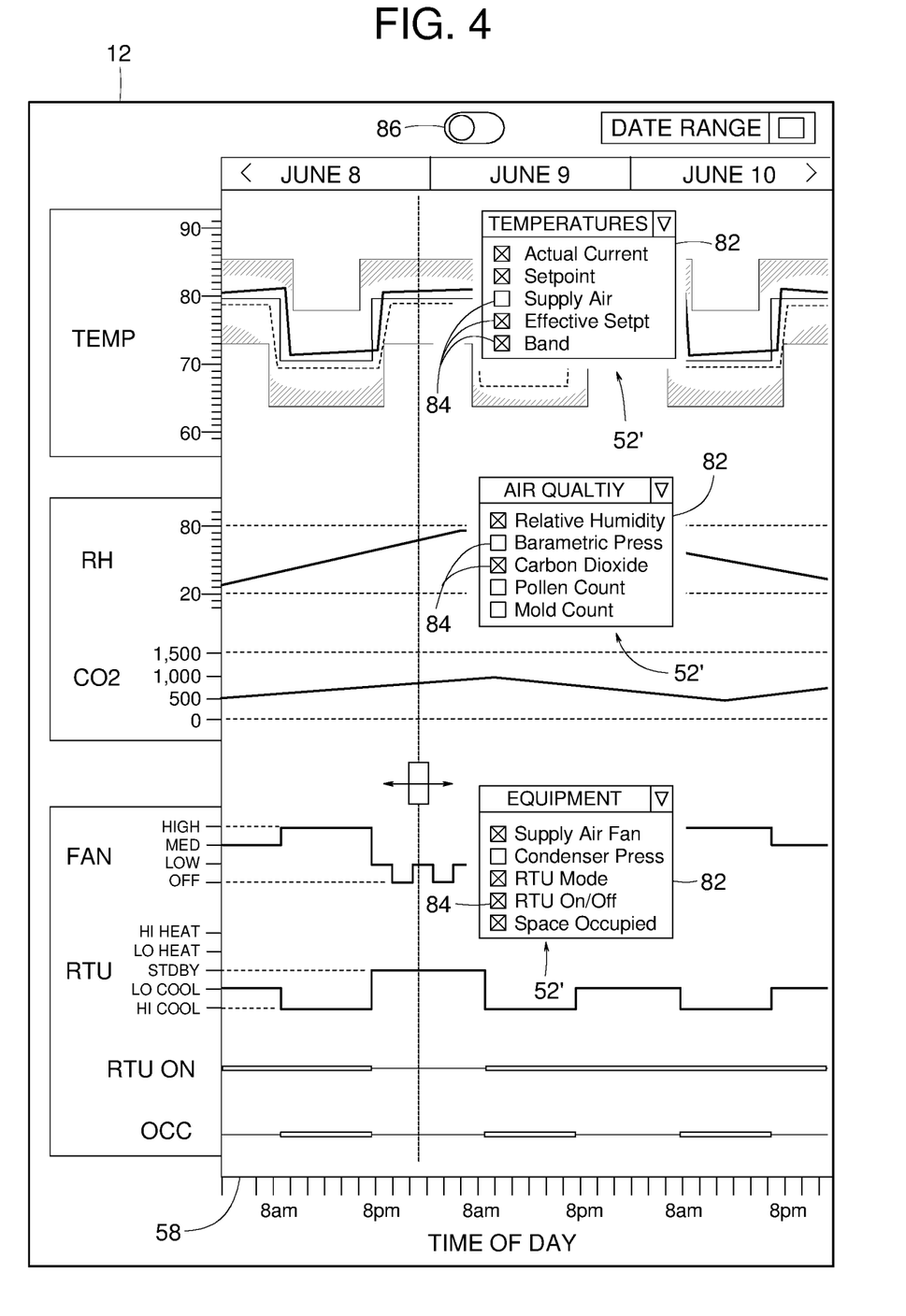
FIG. 4 is another example display screenshot of the computer system shown in FIG. 1.
Figure 5:
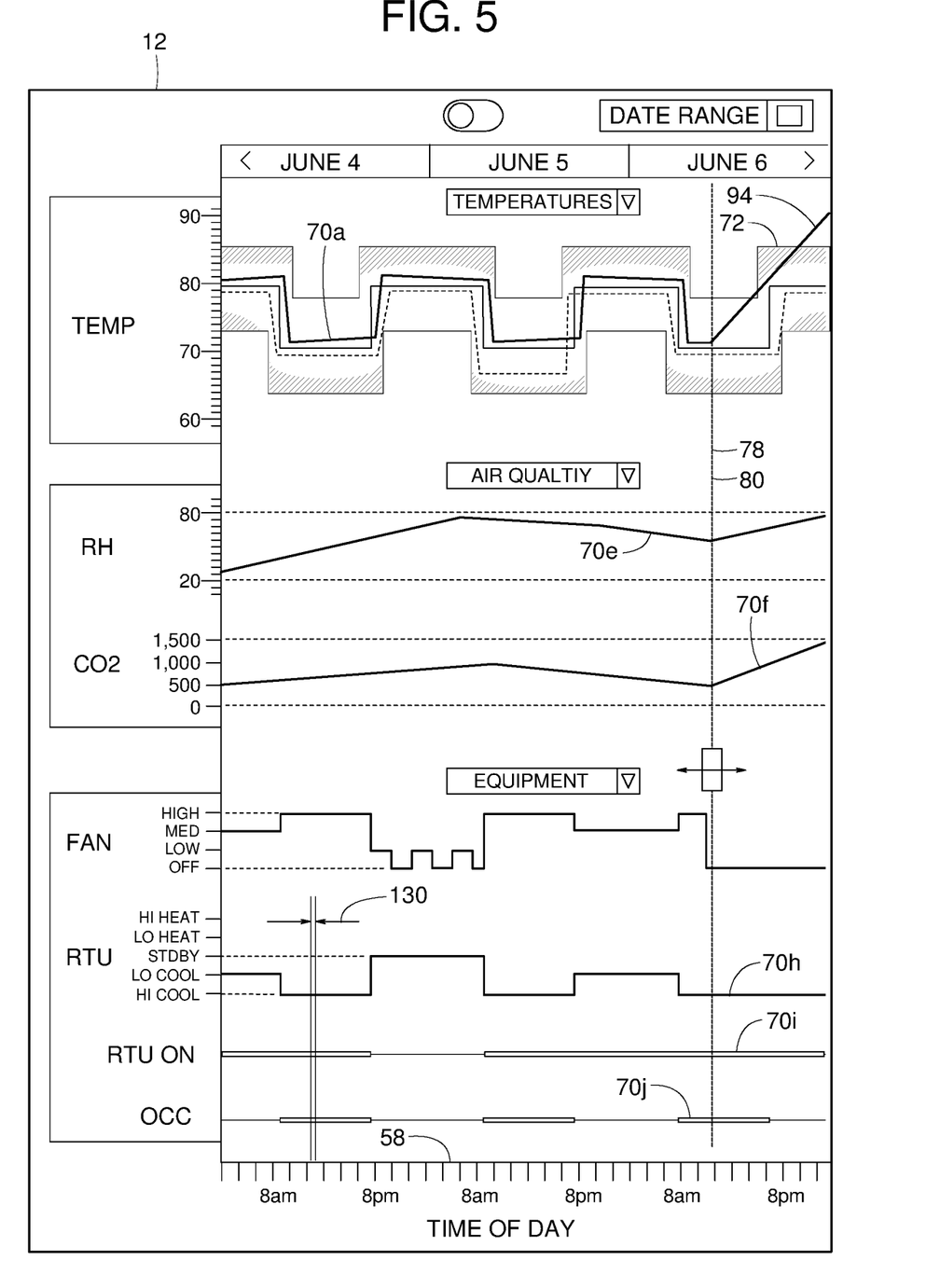
FIG. 5 is another example display screenshot of the computer system shown in FIG. 1.
Figure 6:
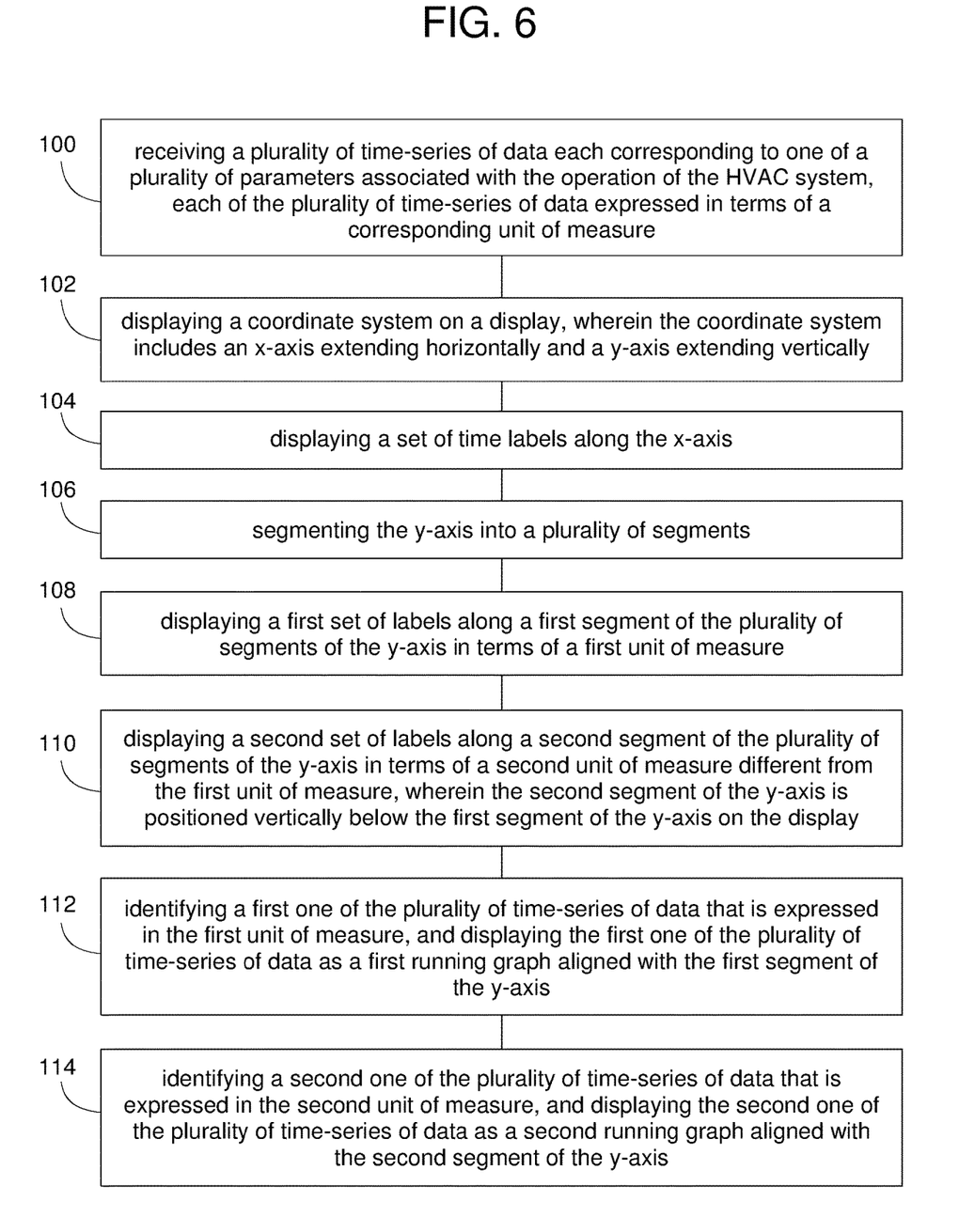
FIG. 6 an example flow diagram illustrating example method steps of the computer system shown in FIG. 1.
Figure 7:
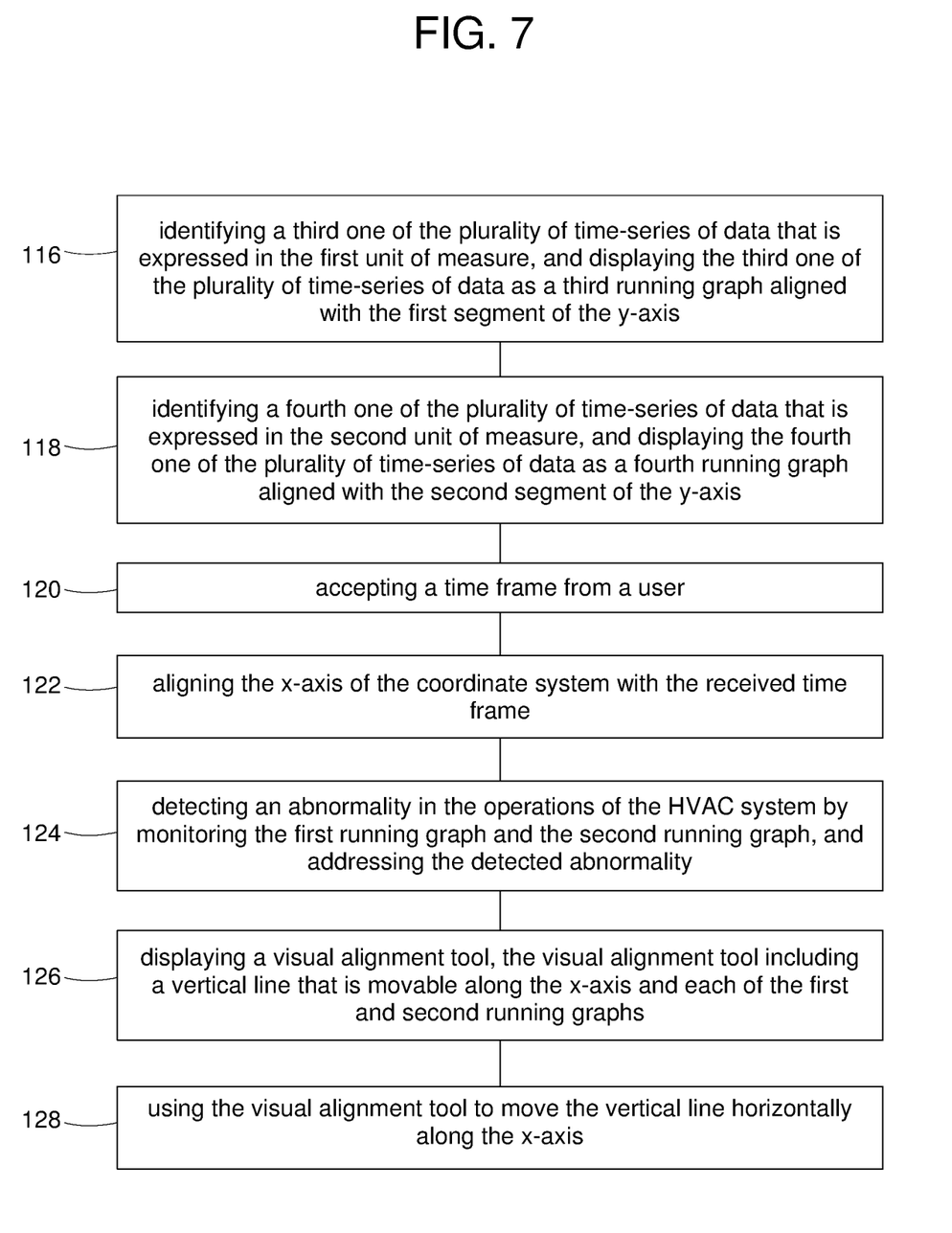
FIG. 7 another example flow diagram illustrating example method steps of the computer system shown in FIG. 1.

FIG. 1 is a schematic diagram of an example computer system 10 (computing system and/or processor) with a display 12 for monitoring the operation of an example HVAC system 14 and/or the conditions of a comfort zone 16 served by HVAC system 14. HVAC refers to heating, ventilating and air conditioning. FIGS. 2-5 illustrate various example screenshots of display 12, and FIGS. 6 and 7 illustrate various method steps associated with computer system 10.

Computer system 10 is schematically illustrated to represent at least one digital device that includes a computer readable medium 18. The term, "computer readable medium" refers to any device for storing information for any duration (e.g., for extended time periods, permanently, for brief instances, for temporarily buffering, for caching of the information, etc). The term, "program code" refers to executable instructions (e.g., computer readable instruction, machine readable instructions, software, etc.). The term, "non-transitory computer readable medium" is specifically defined to include any type of computer readable storage device and/or storage disk and to exclude propagating signals and to exclude transmission media.

In some examples, HVAC system 14 includes a thermostat 20 for providing output signals 22 to control the operation of HVAC system 14. Output signals 22, in some examples, are in response to feedback signals 24 from sensed conditions of comfort zone 16 and/or HVAC system 14. In some examples, output signal 22 varies in response to an input 26 received directly from a user 28 and/or input 30 received indirectly by way of user 28 interacting 32 with a touchscreen version of display 12 and/or some other known computer input device.

The term, "HVAC system," refers to one or more devices for affecting the temperature, humidity and/or ventilation of a comfort zone. Some examples of such devices include an air conditioner, a chiller, a rooftop unit, an air handling unit, a heat pump, a furnace, a boiler, a heat exchanger, an evaporator, a condenser, a fan, a compressor, a damper, an expansion valve, and various combinations thereof. The term, "comfort zone," refers to any designated room, area or space within one or more buildings.

In the example schematically illustrated in FIG. 1, HVAC system 14 includes a rooftop unit 34, sometimes known as an RTU. In some examples, HVAC system 14 includes a refrigerant circuit 36, a compressor 38, two heat exchangers 40 and 42, an expansion valve 44, and a 2-position 4-way valve 46. The position of valve 46 determines the direction of refrigerant flow through circuit 36, and thereby determines whether HVAC system 14 operates in a cooling mode or a heating mode. FIG. 1 happens to show HVAC system 14 in a cooling mode, wherein heat exchanger 42 functions as an evaporator for cooling a supply of air 48. Fan 50 then forces the supply of air 48 to cool comfort zone 16. Such operation and other example modes of operation are well known to those of ordinary skill in the art of HVAC.

In the illustrated example, computer system 10 receives a plurality of time-series data 52 corresponding to a plurality of parameters associated with the operation of HVAC system 14. Time-series data 52 may be provided by thermostat 20, various sensors of HVAC system 14, and/or various sensors associated with comfort zone 16. In some cases, the computer system 10 is located at the building hosting the HVAC system 14. In other cases, the computer system 10 is remote from the building housing the HVAC system 14. In some instances the building housing the HVAC system 14 may include a gateway or the like (not shown) that operatively connects the computer system 10 and the HVAC system 14. In some cases, the computer system is a multi-site Building Monitoring System (BMS) that is configured to monitor HVAC systems at multiple building sites. These are just examples.

Examples of time-series data 52 include an actual current temperature 52a of comfort zone 16, a comfort zone setpoint temperature 52b, an effective setpoint temperature 52c, a predetermined normal operating range band 52d, a comfort zone relative humidity 52e, a comfort zone's concentration of carbon dioxide 52f, a supply air fan operating mode 52g of fan 50, an RTU mode 52h of rooftop unit 34, an RTU on/off status 52i of rooftop unit 34, and a space occupied state 52j indicating whether or not comfort 16 is occupied. Additional examples of time-series data 52 may include a supply air temperature, outside barometric pressure, indoor static pressure, pollen count, mold count, condenser fan pressure, etc.

Each of time-series data 52 can be expressed in terms of a corresponding unit of measure 54 and may be grouped and organized accordingly. Time-series data 52a-d, for example, may be expressed in degrees (e.g., Centigrade or Fahrenheit) and placed in one group. Relative humidity 52e and carbon dioxide 52f may be expressed in percent and placed in another group. In addition or alternatively, carbon dioxide 52f may be expressed in ppm (parts per million) yet kept in the same group as relative humidity 52e. Supply air fan data 52g may be expressed as a selective operating state of high, medium, low and off. RTU mode data 52h may be expressed as selective operating mode of high heat, low heat, standby, low cool and high cool. RTU on/off data 52i may be expressed as being either on or off. Space occupied data 52j may be expressed as comfort zone 16 being either occupied or unoccupied. Time-series data 52g-j can be placed in a third group.

Figure 2:
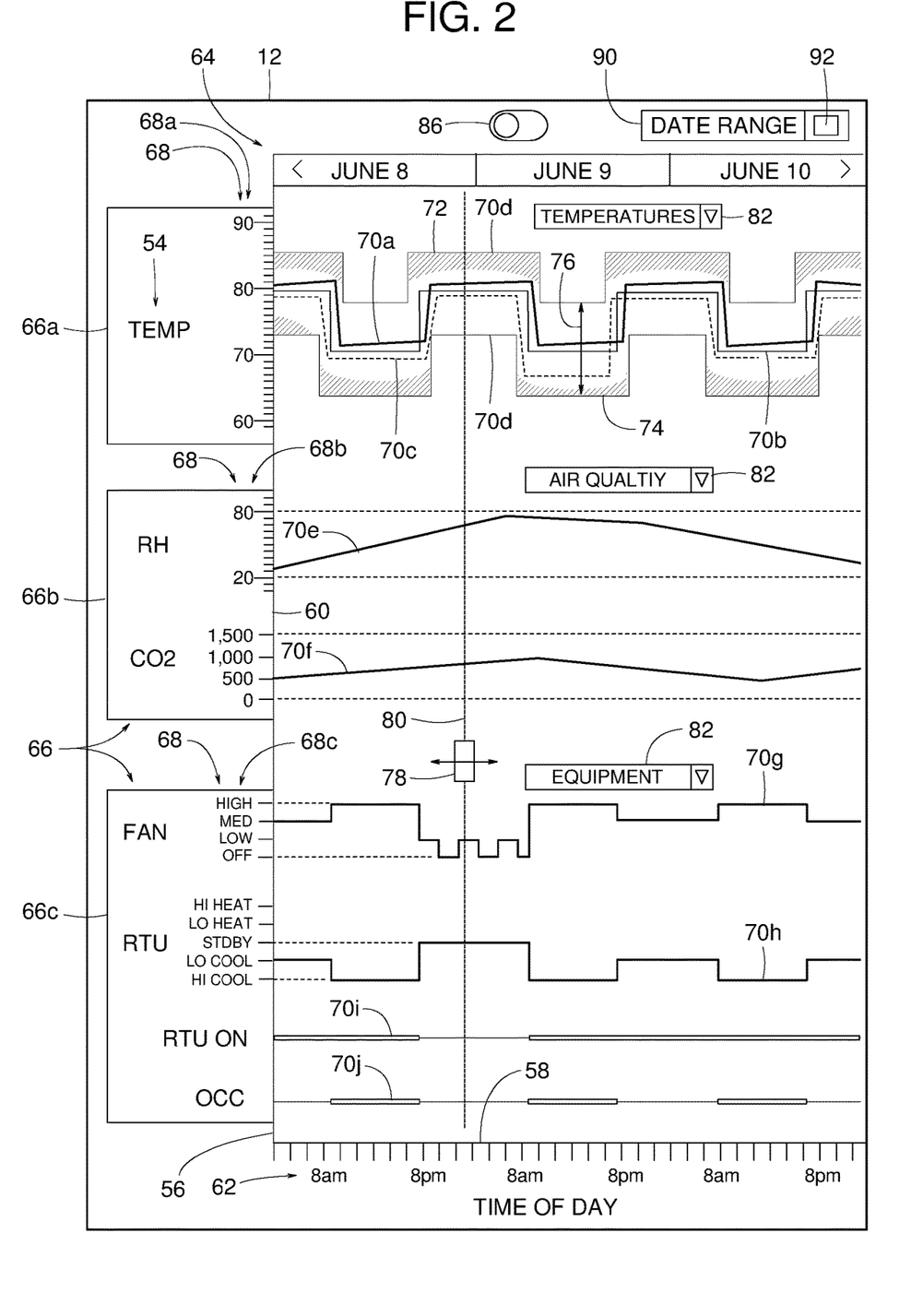
FIG. 2 is an example display screenshot of the computer system shown in FIG. 1.

To analyze data 52 in an efficient, organized manner, some examples of computer system 10 provide a coordinate system 56 on display 12, as shown in FIG. 2. Coordinate system 56 includes a horizontal x-axis 58 and a vertical y-axis 60. X-axis 58 includes a set of time labels 62 indicating the time of day, while in that same section or in another section 64, the date and/or day of the week is displayed. Y-axis 60 includes a plurality of segments 66 (e.g., a first segment 66a, a second segment 66b and a third segment 66c). Segments 66a, 66b and 66c correspond to the groups in which time-series data 52 have been sorted. To easily compare data of multiple segments but at the same particular point in time, segments 66a, 66b and 66c are distributed in a vertically offset arrangement with each segment 66 being aligned directly above or below another.

Each segment 66a, 66b and 66c includes one or more labels 68 with units of measure that differ from the units of measure in the other segments. First segment 66a, for example, includes a first set of labels 68a having temperature as its unit of measure. Second segment 66b includes a set of labels 68b having percent and/or ppm as its units of measure. Third segment 66c includes a set of labels 68c having various other units of measure, such as high, medium, low and off; hi heat, low heat, standby, low cool and high cool; on or off; and occupied or unoccupied.

In the illustrated example, time-series data 52a is displayed as a running graph 70a (actual temperature of comfort zone 16) in first segment 66a. The term, "running graph" refers to a plotted line that continues with time, so for a given fixed time period, only the portion of line that corresponds to that period is visible.

Time-series data 52b is displayed as a running graph 70b (setpoint temperature) in first segment 66a. Time-series data 52c is displayed as a running graph 70a (effective setpoint temperature) in first segment 66a. In some examples, the effective setpoint (running graph 70c) is a little above or below the actual setpoint temperature (running graph 70b) to control HVAC system 14 such that HVAC system 14 drives the actual comfort zone temperature (running graph 70a) more quickly to the setpoint temperature (running graph 70b). In some examples, the effective setpoint (running graph 70c) varies in part as a function of relative humidity (running graph 70e), as sometimes it may desirable to cool comfort zone 16 to less than its setpoint temperature (running graph 70b) to reduce relatively high humidity to a more comfortable level.

Time-series data 52d is displayed as a running graph 70d (predetermined normal temperature band) in first segment 66a. Running graph 70d is a plot of an upper limit 72 and a lower limit 74 of a predetermined normal range 76 of comfort zone temperature. The predetermined normal range 76 may shift depending on whether or not comfort zone 16 is occupied.

Referring to second segment 66b, time-series data 52e is displayed as a running graph 70e (relative humidity of comfort zone 16) in second segment 66b. Time-series data 52f is displayed as a running graph 70f (the comfort zone's concentration of carbon dioxide) in second segment 66b.

Referring to third segment 66c, time-series data 52g is displayed as a running graph 70g (operating mode of fan 50) in third segment 66c. Time-series data 52h is displayed as a running graph 70h (RTU mode) in third segment 66c. Time-series data 52i is displayed as a running graph 70i (RTU on/off state) in third segment 66c. Time-series data 52j is displayed as a running graph 70j (occupancy of comfort zone 16) in third segment 66c.

Plotting running graphs 70a-j one above the other helps user 28 to compare the various parameters at a particular point in time. In some examples, computer system 10 displays a visual alignment tool 78 with a vertical line 80 that is movable along x-axis 58, i.e., vertical line 80 is movable in a direction parallel to x-axis 58. User 28 can move visual alignment tool 78 with its vertical line 80 laterally (horizontally) across running graphs 70a-j to any chosen point in time displayed on x-axis 58. In some examples, user 28 can move visual alignment tool 78 by mouse-clicking and dragging visual alignment tool 78. In examples where display 12 is a touchscreen, user 28 can move visual alignment tool 78 by pointing and dragging on display 12.

Some examples of computer system 10 include dropdown menus 82 with checkboxes 84 for selecting which running graphs 70a-j and/or others are to be displayed on coordinate system 56. FIG. 4 shows names 52' of some example time-series data 52 that may be chosen. Other examples of computer system 10 include more or less time-series data 52' than those listed in FIG. 4.

Figure 3:
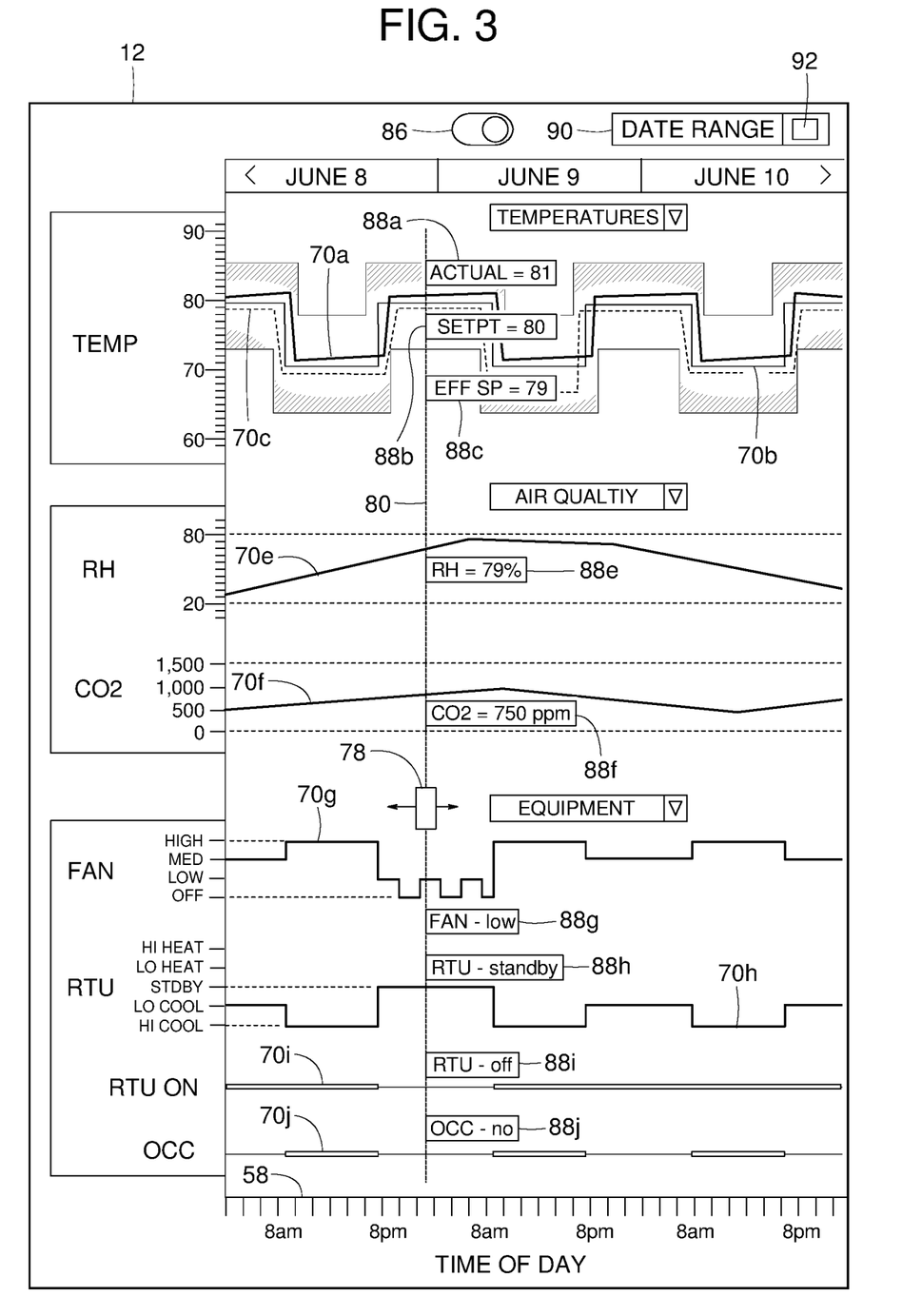
FIG. 3 is another example display screenshot of the computer system shown in FIG. 1.

Referring further to FIG. 3, some examples of system 10 include a virtual switch 86 that provides user 28 with an option of selectively displaying or hiding a plurality of discrete y-axis values 88*a-c* and 88*e-j*. When user 28 moves switch 86 to the position shown in FIG. 2, the plurality of discrete y-axis values 88*a-c* and 88*e-j* are hidden (not shown or displayed). When user 28 moves switch 86 to the position shown in FIG. 3, computer system 10 displays the plurality of discrete y-axis values 88*a-c* and 88*e-j*. Values 88*a-c* and 88*e-j* correspond to where each of running graphs 70*a-c* and 70*e-j* intersects the visual alignment tool's vertical line 80.

Figure 8:
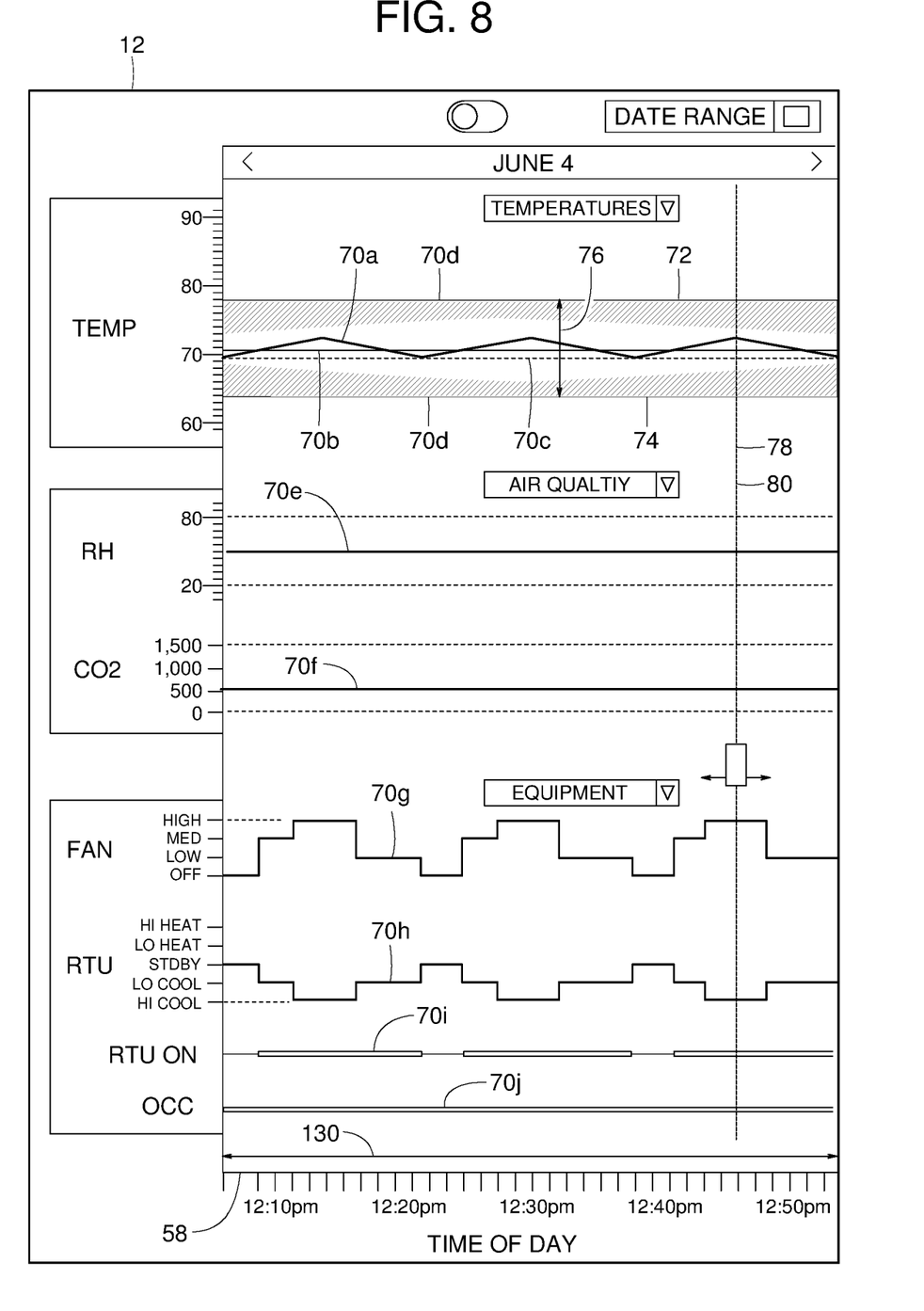
FIG. 8 is another example display screenshot of the computer system shown in FIG. 1.

In some examples, system 10 includes a date range button 90. User 28 can use date range button 90 to define a desired timeframe 92 for x-axis 58. In FIGS. 2-4, for instance, x-axis 58 covers a timeframe of June 8 to June 10. In FIG. 5, x-axis 58 covers a timeframe of June 4 to June 6. In FIG. 8, x-axis 58 covers a timeframe of about one hour near noon June 4.

In the example shown in FIG. 5, display 12 shows an abnormality 94 in the operation of HVAC system 14. Abnormality 94 appears to have started at approximately noon on June 6. At this point in time, running graph 70*a* of the zone's actual temperature appears to be rising abnormally and continues past 8 PM on June 6. The zone's actual temperature eventually exceeds the system's predetermined normal operating range, as indicated by the band's upper limit 72.

While diagnosing the problem, user 28 may readily see that fan 50 abruptly and unexpectedly changed from "high" to "off" just before the zone's actual temperature began its abnormal ascent. User 28 would expect fan 50 to be on for several reasons. One, zone 16 is occupied, as indicated by running graph 70*j* (space occupied). Two, RTU 34 is still running, as indicated by running graph 70*i*. And three, RTU 34 is in its high cooling mode, as indicated by running graph 70*h*.

With RTU 34 running without supply air fan 50 operating, it is not surprising that not only would the zone's temperature rise, but the zone's relative humidity and concentration of carbon dioxide would rise as well. And this seems to be the case, as indicated by running graph 70*e* (relative humidity) and running graph 70*f* (concentration of carbon dioxide). In some examples, user 28 may address the detected problem by servicing supply air fan 50 directly, as indicated by line 96 (FIG. 1). In some examples, system 10 may address the detected problem by sending a corrective control signal 98 to HVAC system 14.

FIG. 6 is a flow diagram illustrating some example steps of an example method for monitoring operations of HVAC system 10. In some examples, blocks 100, 102, 104, 106, 108, 110, 112 and 114 may be performed by computer system 10 and/or user 28.

FIG. 7 is a flow diagram illustrating some example steps of an example method for monitoring operations of HVAC system 10. In some examples, blocks 116, 118, 120, 122, 124, 126 and 128 may be performed by computer system 10 and/or user 28.

FIG. 8 shows the expansion of a very narrow time period 130 taken from axis 58 of FIG. 5. Time period 130, in the illustrated example, is about one hour near noon on June 4. By focusing in on such a short period of time, user 28 can see more detailed fluctuations of running graphs 70*a-j* that might not otherwise be apparent in views of much longer time periods.

The disclosure should not be considered limited to the particular examples described above. Various modifications, equivalent processes, as well as numerous structures to which the disclosure can be applicable will be readily apparent to those of skill in the art upon review of the instant specification.

What is claimed is:

1. A method for monitoring operations of an HVAC system that is used for conditioning air of a comfort zone, the method comprising:
   receiving a plurality of time-series of data each corresponding to one of a plurality of parameters associated with the operation of the HVAC system, each of the plurality of time-series of data expressed in terms of a corresponding unit of measure;
   displaying a coordinate system on a display, wherein the coordinate system includes an x-axis extending horizontally and a y-axis extending vertically;
   displaying a set of time labels along the x-axis;
   displaying a first set of labels along a first segment of a plurality of segments of the y-axis in terms of a first unit of measure;
   displaying a second set of labels along a second segment of the plurality of segments of the y-axis in terms of a second unit of measure different from the first unit of measure, wherein the second segment of the y-axis is positioned vertically above or below the first segment of the y-axis in a non-overlapping manner;
   retrieving and displaying a first one of the plurality of time-series of data as a first running graph aligned with the first segment of the y-axis, wherein the first one of the plurality of time-series of data is expressed in the first unit of measure; and
   retrieving and displaying a second one of the plurality of time-series of data as a second running graph aligned with the second segment of the y-axis, wherein the second one of the plurality of time-series of data is expressed in the second unit of measure;
   displaying a visual alignment tool at a first location along the x-axis, the visual alignment tool includes a vertical line indicator that intersects each of the first and second running graphs at corresponding first locations;
   receiving user input to manually move the visual alignment tool from the first location along the x-axis to a second location along the x-axis; and
   displaying the visual alignment tool at the second location along the x-axis with the vertical line indicator of the visual alignment tool intersecting the first and second running graphs at corresponding second locations.

2. The method of claim 1, further comprising:
   retrieving and displaying a third one of the plurality of time-series of data as a third running graph aligned with the first segment of the y-axis, wherein the third one of the plurality of time-series of data is expressed in the first unit of measure.

3. The method of claim 2, further comprising:
   retrieving and displaying a fourth one of the plurality of time-series of data as a fourth running graph aligned with the second segment of the y-axis, wherein the fourth one of the plurality of time-series of data is expressed in the second unit of measure.

4. The method of claim 1, wherein the first unit of measure is degrees, and the second unit of measure is percentage.

5. The method of claim 1, further comprises displaying a band in the first segment of the y-axis that corresponds to the first one of the plurality of time-series of data, wherein the band represents a normal range for the first one of the plurality of time-series of data.

6. The method of claim 1, further comprising:
   accepting a timeframe from a user; and
   aligning the x-axis of the coordinate system with the received timeframe.

7. The method of claim 1 further comprising detecting an abnormality in the operations of the HVAC system by monitoring the first running graph and the second running graph, and addressing the detected abnormality by sending a corrective control signal to the HVAC system.

8. The method of claim 1, further comprising:
identifying and displaying a plurality of discrete y-axis values of the first and/or second running graphs that correspond to where the vertical line indicator of the visual alignment tool intersects the first and/or second running graphs with the visual alignment tool at the first location along the x-axis; and
after receiving user input to manually move the visual alignment tool from the first location along the x-axis to a second location along the x-axis, identifying and displaying the plurality of discrete y-axis values of the first and/or second running graphs that correspond to where the vertical line indicator of the visual alignment tool intersects the first and/or second running graphs with the visual alignment tool at the second location along the x-axis.

9. The method of claim 8, further comprising:
providing a user selectable an option to selectively display and hide the plurality of discrete y-axis values.

10. The method of claim 1, wherein the first running graph represents a temperature versus time.

11. The method of claim 1, wherein the first running graph represents a temperature set point versus time.

12. The method of claim 11, further comprising displaying a control dead band about the temperature set point versus time.

13. The method of claim 10, wherein the second running graph represents a measure of humidity versus time.

14. The method of claim 10, wherein the second running graph represents a measure of carbon dioxide versus time.

15. The method of claim 1, wherein one or more of the plurality of time-series of data correspond to equipment status of the HVAC system, the method further comprising:
displaying one of the plurality of time-series of data that correspond to equipment status of the HVAC system as a third running graph aligned with a third segment of the plurality of segments of the y-axis, wherein the third segment of the y-axis does not vertically overlap with either the first segment or the third segment.

16. A computer readable medium having stored thereon, in a non-transitory state, a program code for use by a computing system, wherein the program code, when executed, causes the computing system to:
receive a plurality of time-series of data each corresponding to one of a plurality of parameters associated with an operation of an HVAC system, each of the plurality of time-series of data expressed in terms of a corresponding unit of measure;
display a coordinate system on a display, wherein the coordinate system includes an x-axis extending horizontally and a y-axis extending vertically;
display a set of time labels along the x-axis;
display a plurality of vertically arranged non-overlapping segments along the y-axis;
display a first set of labels along a first segment of the plurality of segments of the y-axis in terms of a first unit of measure;
display a second set of labels along a second segment of the plurality of segments of the y-axis in terms of a second unit of measure different from the first unit of measure;
retrieve and display a first one of the plurality of time-series of data as a first running graph aligned with the first segment of the y-axis, wherein the first one of the plurality of time-series of data is expressed in the first unit of measure; and
retrieve and display a second one of the plurality of time-series of data as a second running graph aligned with the second segment of the y-axis, wherein the second one of the plurality of time-series of data is expressed in the second unit of measure;
display a visual alignment tool, the visual alignment tool including a vertical line indicator that is movable along the x-axis and intersects each of the first and second running graphs;
display a plurality of discrete y-axis values of the first and/or second running graphs that correspond to where the first and/or second running graphs intersect the vertical line indicator of the visual alignment tool with the visual alignment tool at a first location along the x-axis;
receive user input to manually move the visual alignment tool to a second location along the x-axis, and thus move the vertical line indicator, horizontally along the x-axis from the first location to a second location along the x-axis; and
display the plurality of discrete y-axis values of the first and/or second running graphs that correspond to where the first and/or second running graphs intersect the vertical line indicator of the visual alignment tool with the visual alignment tool at the second location along the x-axis.

17. The computer readable medium of claim 16, wherein the program code, when executed, causes the computing system to:
retrieve and display a third one of the plurality of time-series of data as a third running graph aligned with the first segment of the y-axis, wherein the third one of the plurality of time-series of data is expressed in the first unit of measure; and
retrieve and display a fourth one of the plurality of time-series of data as a fourth running graph aligned with the second segment of the y-axis, wherein the fourth one of the plurality of time-series of data is expressed in the second unit of measure.

18. The computer readable medium of claim 16, wherein the program code, when executed, causes the computing system to correct abnormalities in the operation of the HVAC system based on user input.

19. A computing system comprising:
a display;
an input for receiving a plurality of time-series of data each corresponding to one of a plurality of parameters associated with an operation of an HVAC system, each of the plurality of time-series of data expressed in terms of a corresponding unit of measure; and
a processor operatively coupled to the display and the input, the processor configured to:
display a coordinate system on the display, wherein the coordinate system includes an x-axis extending horizontally and a y-axis extending vertically;
display a set of time labels along the x-axis;
display a plurality of vertically arranged non-overlapping segments along the y-axis;
display a first set of labels along a first segment of the plurality of segments of the y-axis in terms of a first unit of measure;

display a second set of labels along a second segment of the plurality of segments of the y-axis in terms of a second unit of measure different from the first unit of measure;

retrieve and display a first one of the plurality of time-series of data as a first running graph aligned with the first segment of the y-axis, wherein the first one of the plurality of time-series of data is expressed in the first unit of measure;

retrieve and display a second one of the plurality of time-series of data as a second running graph aligned with the second segment of the y-axis, wherein the second one of the plurality of time-series of data is expressed in the second unit of measure;

retrieve and display a third one of the plurality of time-series of data as a third running graph aligned with the first segment of the y-axis, wherein the third one of the plurality of time-series of data is expressed in the first unit of measure;

retrieve and display a fourth one of the plurality of time-series of data as a fourth running graph aligned with the second segment of the y-axis, wherein the fourth one of the plurality of time-series of data is expressed in the second unit of measure;

retrieve and display one of the plurality of time-series of data that correspond to equipment status of the HVAC system as a fifth running graph aligned with a third segment of the plurality of segments of the y-axis, wherein the third segment of the y-axis does not vertically overlap with either the first segment or the third segment;

display a visual alignment tool, the visual alignment tool including a vertical line indicator that is movable by a user along the x-axis and each of the first and second running graphs;

display a plurality of discrete y-axis values of the first and/or second running graphs that correspond to where the first and/or second running graphs intersect the vertical line indicator of the visual alignment tool with the visual alignment tool at a first location along the x-axis;

accept input from the user that causes the visual alignment tool to move the vertical line indicator horizontally along the x-axis from the first location to a second location along the x-axis;

displaying the plurality of discrete y-axis values of the first and/or second running graphs that correspond to where the first and/or second running graphs intersect the vertical line indicator of the visual alignment tool with the visual alignment tool at the second location along the x-axis;

accept a timeframe from the user; and align the x-axis of the coordinate system with the received timeframe.

* * * * *